US006225516B1

(12) United States Patent
Radici et al.

(10) Patent No.: US 6,225,516 B1
(45) Date of Patent: May 1, 2001

(54) PROCESS FOR THE PRODUCTION OF LINEAR ALKYLAROMATIC HYDROCARBONS

(75) Inventors: Pierino Radici, Turate; Pierluigi Cozzi, Nerviano; Rosanna Ontano, Milan; Agostino Zatta, San Giuliano Milanese, all of (IT)

(73) Assignee: Condea Augusta S.p.A., Palermo (IT)

( * ) Notice: Subject to any disclaimer, the term of this patent is extended or adjusted under 35 U.S.C. 154(b) by 0 days.

(21) Appl. No.: 09/353,062

(22) Filed: Jul. 15, 1999

(30) Foreign Application Priority Data

Jul. 16, 1998 (IT) .............................. MI98A1631

(51) Int. Cl.[7] .............................. C07C 5/00; C07C 2/58; C07C 2/64
(52) U.S. Cl. ..................... 585/323; 585/315; 585/251; 585/252; 585/254; 585/266; 585/448; 585/455
(58) Field of Search .................... 585/315, 323, 585/251, 252, 254, 266, 448, 455

(56) References Cited

U.S. PATENT DOCUMENTS 5,012,021 * 4/1991 Vora et al. ..................... 585/315
5,276,231   1/1994 Kocal et al. ..................... 585/323
5,300,715 * 4/1994 Vora ............................. 585/254

FOREIGN PATENT DOCUMENTS 0 589 511   3/1994 (EP) .

* cited by examiner

Primary Examiner—Walter D. Griffin
Assistant Examiner—Thuan D. Dang
(74) Attorney, Agent, or Firm—Oblon, Spivak, McClelland, Maier & Neustadt, P. C.

(57) ABSTRACT

Process for the production of linear alkylaromatic hydrocarbons comprising:

a) dehydrogenating $C_{10}$–$C_{14}$ n-paraffins;
b) selectively hydrogenating the diolefins produced during step (a);
c) feeding stream (b) and an aromatic hydrocarbon to an alkylation unit;
d) distilling the alkylated stream into its main constituents;
e) subjecting a paraffinic stream containing aromatic by-products, leaving step (d), to a hydrogenation step;
f) recycling the stream leaving step (e) to the dehydrogenation unit of step (a).

20 Claims, No Drawings

PROCESS FOR THE PRODUCTION OF LINEAR ALKYLAROMATIC HYDROCARBONS

BACKGROUND OF THE INVENTION

1. Field of the Invention

The present invention relates to a process for the production of linear alkylaromatic hydrocarbons.

More specifically, the present invention relates to a process for the preparation of linear alkylbenzenes (LAB) containing from 10 to 14 carbon atoms in the alkyl chain.

2. Discussion of the Background

Linear alkylbenzenes, for example containing from 10 to 14 carbon atoms in the alkyl chain, are generally intermediates which are used in the detergent industry.

Processes for the synthesis of linear alkylbenzenes are known in the art. U.S. Pat. No. 5,276,231 describes a process for the preparation of alkylaromatic derivatives, such as LAB, which consists in dehydrogenating a $C_{10}$–$C_{15}$ paraffine stream and alkylating an aromatic compound, for example benzene, with this dehydrogenated stream. Hydrofluoric acid is used as alkylation catalyst.

The by-products obtained in the first dehydrogenation step, essentially of an aromatic nature, are removed by adsorption on molecular sieves or by liquid-liquid extraction, as their presence reduces the activity of the alkylation catalyst and therefore the selectivity to LAB.

SUMMARY OF THE INVENTION

The objective of the present invention is to increase the selectivity of the formation reaction of alkylbenzenes obtained by the continuous alkylation of benzene with mono-olefins coming from the dehydrogenation of n-paraffins and containing, as well as non-converted n-paraffins, the aromatic by-products produced during the dehydrogenation itself. A further objective of the present invention is to increase the selectivity of the dehydrogenation reaction.

The Applicant has now found that these objectives, and others, can be reached by reducing the content of aromatic by-products present in the dehydrogenated stream to values of less than 1.2% by weight of the total in the stream, preferably less than 0.9%, without resorting to particular physical extraction treatment. This result can be obtained by effecting a hydrogenation reaction on the recycled paraffinic stream coming from the alkylation and essentially consisting of paraffins and aromatic by-products as well as, possibly, non-reacted olefins (present in traces).

The hydrogenation reaction of the recycled stream is carried out under particular conditions, as described hereunder, to transform the aromatic by-products into cycloparaffins.

These cycloparaffins are subsequently partly dehydrogenated to cyclo-olefins and act as agents for alkylating the benzene in the alkylation and produce non-linear LAB (iso-LAB). The remaining cycloparaffins that are retransformed into aromatics in this phase, re-enter the cycle but their concentration in the feeding stream of the alkylation reactor is reduced under stationary conditions to values of less than 1.2%, generally less than 0.9%.

U.S. Pat. No. 5,276,231 discloses the possibility of hydrogenating the recycled paraffins. This hydrogenation however substantially has the purpose of eliminating the non-reacted olefins during the alkylation of benzene, as their presence is considered harmful for the dehydrogenation catalyst.

The present invention therefore relates to a process for the production of linear alkylaromatic hydrocarbons, containing from 10 to 14 carbon atoms in the alkyl chain, comprising the following operating cycle:

(a) dehydrogenating $C_{10}$–$C_{14}$ n-paraffins to the corresponding n-olefins obtaining a mixture also comprising diolefins and aromatic by-products as well as light cracking products and hydrogen;

(b) selectively hydrogenating the diolefins formed during step (a) into mono-olefins, obtaining a mixture essentially consisting of mono-olefins and n-paraffins, in addition to the aromatic by-products formed in step (a);

(c) feeding the stream coming from step (b), together with a stream consisting of an aromatic hydrocarbon, to an alkylation unit in which an alkylation catalyst is present;

(d) feeding the alkylation product to a distillation section for the recovery of the excess aromatic hydrocarbon, a paraffinic stream essentially consisting of $C_{10}$–$C_{14}$ n-paraffins and a romatic by-products, and the alkylated aromatic product, respectively;

(e) subjecting the paraffinic stream coming from (d) to a hydrogenation step to transform the aromatic by-products into cycloparaffins;

(f) recycling the stream coming from step (e) to the dehydrogenation unit of step (a).

The $C_{10}$–$C_{14}$ n-paraffins in the charge are preferably introduced into the cycle before step (e).

DESCRIPTION OF THE PREFERRED EMBODIMENTS

Step (a), for the dehydrogenation of n-paraffins, is carried out according to procedures well-known to experts in the field. The reaction is thus effected in the presence of a catalyst comprising a noble metal supported on porous material. The catalyst generally comprises an element of the platinum group in a ratio of 0.01–2% by weight, with respect to the total (catalyst+carrier), an alkaline or earth-alkaline metal in a ratio of 0.1–5% by weight, and it may optionally also contain a constituent selected from one or more of the following metals:

tin: from 0.1 to 1% by weight;

indium: from 0.1 to 1% by weight;

thallium: from 0.1 to 1% by weight.

In the case of the contemporary presence of indium and thallium, these are present in such quantities that the ratio In/Tl is $\geq 0.3$ whereas the ratio Pt/In+Tl is $\geq 1.5$.

In addition, the dehydrogenation reaction of step (a) is carried out at a temperature ranging from 400 to 500° C., at a pressure within the range of 0.1 to 10 kg/cm$^2$ and with a space velocity (LHSV) ranging from 0.1 to 100 h$^{-1}$.

The dehydrogenation reaction preferably takes place in the presence of hydrogen, with a molar ratio hydrogen/n-paraffins ranging from 0.5 to 20, and only partially to reduce secondary cracking and isomerization reactions and the formation of by-products such as diolefins and aromatic hydrocarbons.

At the end of the dehydrogenation reaction the stream essentially consists of linear mono-olefins (10–20% by weight), small quantities of non-linear olefins (generally less than 3% by weight), aromatic by-products (0.1–0.7% by weight), diolefins (0.5–3% by weight) and non-reacted n-paraffins.

During the above step (a) for the dehydrogenation of n-paraffins to olefins, significant quantities of diolefins are therefore formed. Their extent is entirely linked to the conversion and conditions under which the dehydrogenation is carried out. Their presence subsequently leads, during the alkylation step (c), to the formation of impurities such as, for example, tetralines in the alkylbenzenes and heavy, high-boiling products such as, for example, diphenylalkanes, tetralines and indanes with a higher molecular weight.

In order to reduce the disadvantages mentioned above, a selective hydrogenation of the diolefins, step (b) of the process of the present invention, to mono-olefins, is consequently effected.

Step (b) for the selective hydrogenation of the diolefins is carried out on a fixed-bed catalyst based on nickel supported on alumina, partially poisoned, or on a catalyst based on noble metals such as palladium supported on carbon or alumina. In any case, the ratio $H_2$/diolefins is maintained at more than 1 and, generally, between 1.1 and 5, depending on the catalyst used and the process conditions selected.

The above step (b) can be carried out at a temperature ranging from 50 to 250° C. depending on the type of catalyst used and at a pressure ranging from 1 to 20 kg/cm², whereas the space velocity of the flow can vary from 0.5 to 20 $h^{-1}$. In this way, conversion yields of the diolefins of up to 100% are obtained with a selectivity of up to 90%.

The alkylation reaction, step (c) of the process of the present invention, is carried out after mixing the reagents with the alkylation catalyst. Any aromatic hydrocarbon can be used in the alkylation process of the present invention even if benzene and toluene are preferred.

Catalysts which can be used for the purpose are those traditionally used in this type of reaction, for example HF or $AlCl_3$ or solid catalysts of an acidic nature (heterogeneous).

The quantity of catalyst used generally ranges from 0.05% to 10% in moles with respect to the olefin whereas the molar ratio aromatic (benzene)/olefin is between 1 and 20, preferably between 3 and 15.

The alkylation reaction of step (c) is generally carried out at a temperature ranging from 20 to 160° C., at a pressure ranging from 1 to 20 kg/cm², for times varying from 5 to 180 minutes.

At the end of the alkylation reaction a mixture is obtained, essentially consisting of alkylated product, paraffins and by-products coming from both the dehydrogenation and alkylation reactions. This mixture is consequently treated for the recovery of the alkylated product.

The stream leaving the alkylation step is sent to a distillation section from which LAB is recovered with a purity of more than 99%.

The linear alkylbenzene obtained according to the process of the present invention has improved characteristics in terms of purity and overall linearity. The content of cyclic compounds such as dialkyltetralines and dialkylindanes is reduced to values of less than 1% by weight, generally less than 0.5%.

The excess aromatic hydrocarbon, recycled to the alkylation reactor, a paraffinic stream also containing the aromatic by-products formed during the dehydrogenation reaction (step (a) of the present invention) and a stream of high-boiling secondary products, are recovered from the distillation section.

The high-boiling products prevalently consist (>80%) of polyalkylates having a molecular weight >350, with a high fraction of dialkylates having a molecular weight >360. These products can be used as such, for example as auxiliaries in the textile industry, or they can be subjected to further transformation and used as sulfonic acids with a high molecular weight in the lubricating field.

The non-reacted n-paraffins during the dehydrogenation step and the aromatic by-products formed during the same reaction are recovered from the distillation section. These aromatic products consist of at least 75% by weight of alkyl and polyalkylbenzenes and compounds with tetralinic and naphthalenic rings.

The paraffinic stream is recycled to the dehydrogenation. To avoid the accumulation of the aromatic by-products in the cycle, these are hydrogenated to the corresponding cyclo-paraffins in an appropriate unit.

This second hydrogenation generally takes place with a fixed-bed catalyst under percolation conditions (trickle-bed) or immersed in the reagent liquid, even if there is also the possibility of operating in vapour phase.

The catalysts and operating conditions can be selected by the expert in the field on the basis of his own experience and preferred technologies. In any case, the objective to be reached is the highest possible transformation of the aromatic by-products (at least higher than 90%).

For example, in the case of a "trickle-bed" reactor, the hydrocarbon stream and hydrogen are in "down-flow" equi-current at a pressure ranging from 1 to 100 Kg/cm², preferably between 15 and 50 Kg/cm², and a space velocity, calculated on the liquid charge at 20° C., ranging from 1 to 80 $h^{-1}$, preferably between 10 and 40 $h^{-1}$. The quantity of hydrogen is calculated on the stoichiometric value of the reaction with an excess equal to 20–30% in moles.

The temperature can vary, depending on the catalyst, from 50 to 500° C., preferably between 100 and 250° C.

The hydrogenation catalyst consists of one or more metal components or their salts. These metals are selected from those belonging to group VIII and IVA of the periodic table of elements. Preferred metals, however, are nickel, platinum and palladium.

The metal components are supported on inorganic inert materials such as alumina, silica, or their mixtures, clays, synthetic or natural zeolites, etc., in the physical form of cylinders, spherules, extruded products, etc.

The reaction conditions of the hydrogenation phase of step (e) are deliberately more forced that those required for saturating olefinic double bonds. Consequently these, if present, are hydrogenated before the aromatic compounds.

EXAMPLES

A few illustrative examples are provided for a better understanding of the present invention and for its embodiment but in no way limit the scope of the invention itself.

The bromine index is measured according to ASTM D 1491, the Acid Wash Colour according to ASTM D 848-62.

EXAMPLE 1

A pilot plant operating with the same operating steps as an industrial plant, consists of the following basic units for the production of linear alkylbenzene:

- dehydrogenation reactor of n-paraffin;
- selective hydrogenation reactor of diolefins;
- alkylation reactor;
- distillation column capable of recovering the benzene and non-reacted paraffins from the linear alkylbenzene and high-boiling products formed;
- system for the regeneration of the hydrofluoric acid used as alkylation catalyst;
- removal unit of the organic fluorides present in the recycled paraffins;
- additional hydrogenation reactor capable of hydrogenating the olefinic unsaturations and aromatic compounds present in the mixture sent to the dehydrogenation reactor, consisting of charging n-paraffins and recycled paraffins.

A gaseous mixture of $C_{10}$–$C_{13}$ n-paraffins and hydrogen in a molar ratio 1/8 is sent, at a temperature of 485° C., at a pressure of 2 Kg/cm$^2$ and an hourly space velocity, evaluated on the liquid paraffin, of 21 hours $^{-1}$ (paraffin volume/catalyst volume per hour), to a tubular reactor containing, for a height of 250 mm, a solid dehydrogenation catalyst.

The mixture leaving the dehydrogenation reactor, after cooling and separation of the hydrogen, is sent to a reactor containing a selective hydrogenation catalyst of diolefins consisting of 0.35% of palladium supported on alumina. The feeding mixture is regulated so as to have a molar ratio hydrogen/diolefin equal to 1.35. The reactor has a ratio height/diameter equal to 8/1 and operates at a temperature of 120° C. and a pressure of 15 Kg/cm$^2$. Maintaining an LHSV space velocity of 5 h$^{-1}$, the mixture leaving the head of the reactor has, under regime conditions, the following weight composition:

| (HPLC Analysis - RI Detector): | |
|---|---|
| | % |
| Saturated products | 87.1 |
| Mono-olefins | 12.0 |
| Diolefins | <0.1 |
| Aromatics | 0.8 |

Bromine number: 11.65 (g Br/100 g) the $C_{10}$–$C_{13}$ n-paraffin fed to the plant, having the following composition:

| | % |
|---|---|
| $C_{10}$ | 10.3 |
| $C_{11}$ | 31.4 |
| $C_{12}$ | 30.5 |
| $C_{13}$ | 26.4 |
| $C_{14}$ | 0.7 |
| Isoparaffins | 0.45 |
| Aromatics | 0.25 |

The hydrocarbon mixture containing olefins is sent to a cylindrical alkylation reactor after mixing with benzene so as to obtain the following weight ratios:

| hydrocarbon mixture: | 68 parts |
|---|---|
| benzene: | 31.2 parts. |

This mixture is put in contact, on the bottom of the reactor, with 140 parts of hydrofluoric acid at 99.6%. The reactor is equipped with a stirrer, thermo-couple, cooling coil and pressure indicator. The reaction mass has a residence time in the reactor of 60 minutes, at a temperature of 50° C. and a pressure of 4 Kg/cm$^2$. At the outlet of the reactor, the mixture is sent to a separator where the upper organic part and that consisting of the acid are continuously removed. The level is regulated in this container so as to obtain an average residence time of 1.5 hours.

The organic phase is then subjected to fractionated distillation in three successive columns in order to separate, one after another, the benzene and recycled paraffin from the mixture of alkylated products consisting of $C_{10}$–$C_{13}$ alkylbenzenes and heavy alkylated products.

The recovered benzene, after integration with fresh benzene, is sent for alkylation whereas fresh paraffin is added to the recycled paraffin, after passage on active alumina at a temperature of 190° C. to eliminate the organic fluorine, which is sent to a hydrogenation reactor for the saturation of the aromatic compounds.

The cylindrically-shaped reactor, with a ratio height/diameter of 5, contains a catalyst with an active base of nickel (20%) supported on alumina, consisting of extruded products having a dimension of 1.2 mm in diameter and 3 mm in length. A mixture of paraffin and hydrogen is fed to this reactor, from the top downwards. The operating conditions are the following:

space velocity of the liquid: 25 h$^{-1}$ temperature: 160° C.

pressure: 20 Kg/cm$^2$ $H_2$/aromatics: 3.65 mol.

The catalytic system operates in trickle-bed. The analyses of the products at the inlet and outlet are the following:

| | Inlet | Outlet |
|---|---|---|
| | % | % |
| Aromatics | 0.83 | 0.04 |
| N-paraffins | 97.07 | 97.07 |
| Other paraffins | 2.10 | 2.89 |
| Bromine index (mgBr/100 g) | 10 | <10 |

The paraffinic stream is then sent back to the dehydrogenation reactor.

The alkylated product is subjected to distillation to separate the $C_{10}$–$C_{13}$ alkylbenzene from the heavy alkylated products. The analytical results and applicative characterization of the LAB product after direct sulfonation are summarized in tables 1 and 2.

The -heavy alkylated products have the compositional characteristics indicated in table 3.

Table 4 indicates the quantitative data of the production of heavy alkylated products and polymeric products separated from the recovery-purification of hydrofluoric acid.

Example 2 (comparative)

For the production of linear alkylbenzene, the same n-paraffin is fed to the plant of example 1 where the hydrogenation process unit of the mixture of recycled and also reintegrating paraffins, before the dehydrogenation reaction, is eliminated.

The process conditions of the single reaction units (dehyrogenation, hydrogenation of diolefins and alkylation) and separation units. of benzene, linear alkylbenzene and heavy alkylated products are kept identical to those of example 1.

The analysis and characterization results are summarized in tables 1–4.

Internal control of the process units gave the following analytical results of the hydrocarbon stream at the inlet of the alkylation reactor:

| HPLC analysis - RI detector | |
|---|---|
| | % |
| Saturated products | 83.4 |
| Mono-olefins | 11.9 |
| Diolefins | 0.1 |
| Aromatics | 4.6 |

Bromine number: 11.6

The paraffins at the inlet of the dehydrogenation reactor, consisting of recycled and fresh reintegrating paraffins, have the following analytical data under stationary conditions:

| | % |
|---|---|
| n-Paraffins | 93.12 |
| Other paraffins | 2.55 |
| Aromatics | 4.33 |

TABLE 1

LAB ANALYSES

| Gas-Chromatography | Ex. 1 (%) | Ex. 2 (Comp) (%) |
|---|---|---|
| $C_{10}$–$C_{13}$ n-phenyl | 93.8 | 93.0 |
| Tetralines | 0.3 | 0.5 |
| iso-alkylbenzenes | 6.1 | 5.9 |
| Diphenyls | <0.1 | 0.6 |
| 2-n-phenylisomers | 17.7 | 17.3 |
| Bromine index | <5 | 6 |

TABLE 2

LAS ANALYSES

| | Ex. 1 (%) | Ex. 2 (Comp) (%) |
|---|---|---|
| Active matter | 97.6 | 95.3 |
| Free acidity | 1.0 | 1.5 |
| Disulfonates | <0.1 | 0.6 |
| Klett colour | 10 | 35 |

TABLE 3

Analyses of heavy alkyates

| | Ex. 1 % | Ex. 2 (Comp) % |
|---|---|---|
| Gas Chromatography | | |
| Residual LAB | 5.2 | 6.2 |
| Mass Analysis (molar %) | | |
| Polyalkylbenzenes | 83.4 | 63.5 |
| Naphthalenes | 1.8 | 6.7 |
| Dinaphthene naphthalenes | 2.4 | 5.8 |
| Dinaphthenebenzenes | 2.8 | 4.7 |
| Diphenylalkanes | 3.5 | 6.6 |
| Tetralines-Indanes | 7.1 | 12.7 |
| Molecular weight | 375 | 338 |

TABLE 4

| | parts by weight/1000 parts LAB | |
|---|---|---|
| | Ex. 1 | Ex. 2 (Comp) |
| Heavy alkylated products/LAB | 38 | 75 |
| Polymers/LAB | 9 | 28 |
| Light products + $H_2$/LAB | 75 | 95 |
| HF (Consumption) | 0.18 | 0.3 |

Example 3

Normal $C_{10}$–$C_{13}$ paraffins of example 1 are fed to a plant for the production of linear alkylbenzene LAB comprising the same units as example 1 except for the alkylation unit. This is substituted with another unit suitable for the use of $AlCl_3$ as alkylation catalyst. The reactor, equipped with a stirrer, is cylindrical with a ratio height/diameter of 5. It is also equipped with separator septa installed at a regular distance and with a central hole equal to 40% of the diameter of the reactor itself. An external jacket, with water circulation, allows thermostat-regulation at the desired temperature.

A gaseous mixture of n-paraffins and hydrogen, molar ratio n-paraffin/$H_2$ of 1/10, is sent to the dehydrogenation reactor maintained at a temperature of 485° C. and a pressure of 1.9 Kg/cm². The hourly space velocity of the paraffin, LHSV, is equal to 32 $h^{-1}$, evaluated as liquid flow-rate. The outgoing mixture after separation of the hydrogen and cooling, is sent to the selective hydrogenation reactor, the hydrogen added being regulated so as to maintain a molar ratio between hydrogen and diolefins equal to 1.35. The hydrocarbon mixture at the outlet, whose analysis is the following:
(HPLC analysis—RI detector):

| | % |
|---|---|
| Saturated products | 89.2 |
| Mono-olefins | 11.0 |
| Diolefins | <0.1 |
| Aromatics | 0.7 |

Bromine number: 10.65 (g Br/100 g) is sent to the alkylation reactor after mixing with benzene and the catalyst ($AlCl_3$)

After a residence time of 1 hour at a temperature of 55° C. in the reactor, the reaction mixture is discharged in continuous and is left to decant in a nonstirred cylindrical container with a capacity that is such as to guarantee a residence time of 2 hours. The alkylation mixture separated from the catalyst has the following composition (parts by weight):

| | |
|---|---|
| Hydrocarbon mixture | 68 |
| Benzene | 30.9 |
| $AlCl_3$ | 0.12 |
| Catalytic complex | 2 |
| HCl | 0.008 |
| High-boiling alkyated products | 4 |

The organic part is washed with an aqueous solution of NaOH at 3% and subsequently with water. After decanting, the organic mixture is separated into its components by distillation, as in example 1.

The linear alkylbenzene and heavy alkylated products are subjected to analysis, of which the results are indicated in tables 5 and 6 respectively.

The paraffin recycled from the distillation, containing 12 ppm of chlorine, is percolated in a tubular reactor having a ratio height/diameter of 5, containing a cylindrical solid adsorber having a diameter of 1/16" consisting of alumina and calcium oxide (20%), at a temperature of 220° C. and a space velocity of 3 h−1. Charges of n-paraffin and hydrogen are added to the outgoing product, before being introduced into the hydrogenation unit of example 1. The operating conditions and analytical results of the streams are the following:

Temperature: 150° C.

Pressure: 20 Kg/cm$^2$

LHSV calculated at 20° C.: 20 h$^{-1}$

H$_2$/Aromatics: 3.75 (molar)

Analysis

|  | Inlet % | Outlet % |
|---|---|---|
| Aromatics | 0.7 | 0.03 |
| N-paraffins | 97.0 | 97.0 |
| Other paraffins | 2.3 | 2.97 |
| Bromine index (mgBr/100 g) | 10 | <10 |

Hydrogen is added to the outgoing mixture up to a molar ratio of 1/10, which is again sent to the dehydrogenation reactor.

The productions of heavy alkylated products and consumptions, under regime conditions, are indicated in table 7.

Example 4 (Comparative)

For the production of linear alkylbenzene, the same n-paraffin as example 1 is fed to the plant of example 3, where the hydrogenation process unit of the mixture of paraffins before entering the dehydrogenation inlet, is eliminated. The process conditions of the single reaction units (dehydrogenation, selective hydrogenation of diolefins and alkylation) and separation of the benzene, recycled paraffins, linear alkylbenzene and heavy alkylated products, are identical to those of example 3.

The paraffins entering the dehydrogenation reactor, consisting of recycled and fresh reintegrating paraffins have the following analytical data, under stationary conditions:

|  | % |
|---|---|
| n-Paraffins | 92.8 |
| Other paraffins | 2.4 |
| Aromatics | 4.8 |

The results of the analyses and balances are indicated in tables 5–7.

TABLE 5

LAB ANALYSES

| Gas-Chromatography | Ex. 3 % | Ex. 4 (Comp) % |
|---|---|---|
| C$_{10}$–C$_{13}$ n-phenyl | 96.9 | 96.0 |
| Tetralines | 0.4 | 1.0 |
| iso-alkylbenzenes | 2.7 | 2.8 |
| 2-n-phenylisomers | 30.1 | 30.0 |
| Bromine index | 10 | 60 |
| Acid Wash Colour | 9 | 11.5 |

TABLE 6

Analyses of heavy alkyates

|  | Ex. 3 % | Ex. 4 (Comp) % |
|---|---|---|
| Gas Chromatography Residual LAB | 3.6 | 3.7 |
| Mass Analysis (molar %) |  |  |
| Polyalkylbenzenes | 91.5 | 80.3 |
| Naphthalenes | 0.2 | 2.3 |
| Dinaphthenebenzenes | 0.6 | 4.8 |
| Diphenylalkanes | 1.7 | 3.2 |
| Tetralines-Indanes | 6.2 | 9.4 |
| Molecular weight | 390 | 356 |

TABLE 7

| | parts by weight/1000 parts LAB | |
|---|---|---|
|  | Ex. 3 | Ex. 4 (Comp) |
| Heavy alkylated products/LAB | 40.8 | 85 |
| AlCl$_3$/LAB | 11.3 | 11.8 |
| HCl/LAB | 0.8 | 0.85 |

Example 5

The normal paraffins of example 1 are fed to a plant for the preparation of linear alkylbenzene LAB containing the same units as example 1 except for the alkylation unit and recovery of the hydrofluoric acid.

This alkylation unit is substituted with a reactor containing a solid catalyst consisting of ultrastable Y zeolite supported on clay. The catalyst is extruded form having a diameter of 1.58 mm and a length of 2–5 mm.

The steel reactor has a ratio height/diameter of 8/1 and is able, by means of an exchanger situated at the inlet and an external jacket, to effect thermostat-regulation at the desired temperature.

Operating, for all the other units, under the same conditions as example 3, the hydrocarbon mixture containing the olefin is introduced into the reactor after mixing with benzene. The hydrocarbon composition under regime is the following:

HPLC analysis—RI detector

|  | % |
|---|---|
| Saturated products | 88.1 |
| Mono-olefins | 11.0 |

-continued

|  | % |
|---|---|
| Diolefinis | 0.1 |
| Aromatics | 0.8 |

The ratio between the olefin and benzene is equal to 1/15 in moles.

The mixture is maintained liquid, at a temperature of 125° C. and a pressure of 30 Kg/cm$^2$, in the reactor where it has a residence time of 60'. Under stationary conditions, the catalyst has a life of 220 hours with a conversion of the olefin of more than 99.9% (bromine index of the outgoing mixture less than 5 mg Br/100 g).

The outgoing organic mixture is then separated into its components by distillation analogously to the previous cases. The linear alkylbenzene and heavy alkylated products are subjected to analysis, of which the results are summarized in tables 8 and 9.

Hydrogen is added to the recycled paraffin, after mixing with the charge of n-paraffin, which is introduced into the hydrogenation unit of example 1. The operating conditions and analytical results of the streams are as follows:

space velocity of the liquid: 25 h$^{-1}$;

temperature: 160° C.

pressure: 20 Kg/cm$^2$

H$_2$/Aromatics: 3.75 mol.

Analysis

|  | Inlet % | Outlet % |
|---|---|---|
| aromatics | 0.7 | 0.03 |
| n-paraffins | 97.0 | 97.0 |
| other paraffins | 2.3 | 2.97 |
| Bromine index (mgBr/100 g) | 20 | <10 |

Hydrogen is added to the mixture leaving the reactor up to a molar ratio mixture/H$_2$ equal to 1/10 which is again sent to the dehydrogenation section.

Under stationary conditions, the productions of heavy alkylated products are indicated in table 10.

Example 6 (Comparative)

For the production of linear alkylbenzene, the n-paraffin of example 1 is fed to the plant of example 5, where the hydrogenation process unit of the mixture of paraffins before entering dehydrogenation, is eliminated. The process conditions of the single reaction units (dehydrogenation, selective hydrogenation of diolefins and alkylation) and separation of the benzene, recycled paraffins, linear alkylbenzene and heavy alkylated products, are identical to those of example 3.

Under stationary conditions, the paraffins entering the dehydrogenation reactor have the following composition:

|  | % |
|---|---|
| n-Paraffins | 93.0 |
| Other paraffins | 2.0 |
| Aromatics | 4.4 |
| Bromine index | 27 |

The hydrocarbon mixture entering the alkylation section has the following composition:

| HPLC analysis - RI detector | |
|---|---|
|  | % |
| Saturated products | 84.1 |
| Mono-olefins | 10.8 |
| Diolefins | <0.1 |
| Aromatics | 4.7 |

The alkylation catalyst has, under the same operating and flow conditions, an active life of 65 hours with a conversion of the olefin equal to 99.9%. The results of the analyses and balances are summarized in tables 8–10.

TABLE 8

| LAB ANALYSES | | |
|---|---|---|
| Gas-Chromatography and mass | Ex. 5 % | Ex. 6 (Comp) % |
| $C_{10}$–$C_{13}$ n-phenyl | 93.5 | 93.3 |
| Tetralines | 0.1 | 0.3 |
| iso-alkylbenzenes | 6.2 | 6.2 |
| 2-n-phenylisomers | 18.5 | 18.5 |
| Bromine index | <10 | <10 |
| Acid Wash Colour | 12 | 18 |

TABLE 9

| Analyses of heavy alkyates | | |
|---|---|---|
|  | Ex. 5 % | Ex. 6 (Comp) % |
| Gas Chromatography | | |
| Residual LAB | 5.7 | 6.0 |
| Mass Analysis (molar %) | | |
| Polyalkylbenzenes | 82.6 | 61.2 |
| Naphthalenes | 1.9 | 6.9 |
| Dinaphthene naphthalenes | 2.7 | 6.5 |
| Dinaphthenebenzenes | 3.0 | 5.3 |
| Diphenylalkanes | 2.1 | 9.3 |
| Tetralines-Indanes | 7.7 | 9.3 |
| Molecular weight | 383 | 342 |

TABLE 10

| | parts by weight/1000 parts LAB | |
|---|---|---|
|  | Ex. 5 | Ex. 6 (Comp) |
| Heavy alkylated products/LAB | 50.3 | 94.8 |
| Light products + H$_2$ | 74 | 98 |

What is claimed is:

1. A process for producing linear alkylaromatic hydrocarbons containing from 10 to 14 carbon atoms in the alkyl chain, comprising the steps of:
   (a) dehydrogenating $C_{10}$–$C_{14}$ n-paraffins to the corresponding n-olefins in a dehydrogenation reactor to obtain a mixture comprising said n-olefins, diolefins, aromatic by-products;
   (b) selectively hydrogenating said diolefins into mono-olefins, to obtain a mixture comprising said n-olefins said mono-olefins, n-paraffins, and said aromatic by-products;
   (c) feeding said mixture in step (b), together with a stream consisting of an aromatic hydrocarbon, to an alkylation unit in which an alkylation catalyst is present and alkylating to obtain an alkylation product;

(d) distilling said alkylation product to obtain a fraction comprising said aromatic hydrocarbon, a paraffinic fraction consisting essentially of $C_{10}$–$C_{14}$ n-paraffins and said aromatic by-products, and a fraction comprising said linear alkylaromatic hydrocarbons, respectively;

(e) subjecting said paraffinic fraction to a hydrogenation step to transform the aromatic by-products into cycloparaffins;

(f) recycling said cycloparaffins in step (e) to the dehydrogenation reactor of step (a).

2. The process according to claim 1, wherein said dehydrogenating of the n-paraffins is carried out in the presence of a dehydrogenation catalyst comprising a noble metal supported on porous material.

3. The process according to claim 2, wherein the dehydrogenation catalyst comprises an element of the platinum metal group in a ratio of 0.01–2% by weight, with respect to the total, an alkaline or earth-alkaline metal in a ratio of 0.1–5% by weight, and optionally one or more of the following metals:

tin: from 0.1 to 1% by weight;

indium: from 0.1 to 1% by weight;

thallium: from 0.1 to 1% by weight.

4. The process according to claim 3, wherein said of indium and thallium are present in such quantities that the molar ratio In/Tl is $\geqq 0.3$ whereas the molar ratio Pt/In+Tl is $\geqq 1.5$.

5. The process according to claim 1, wherein said dehydrogenating takes place in the presence of hydrogen, with a molar ratio hydrogen/n-paraffins ranging from 0.5 to 20.

6. The process according to claim 1, wherein said selectively hydrogenating is carried out on a fixed bed catalyst comprising nickel supported on alumina, or on a catalyst comprising noble metals supported on carbon, and with a molar ratio hydrogen/n-paraffins with a ratio $H_2$/diolefins higher than 1.

7. The process according to claim 1, wherein said alkylation catalyst is selected from the group consisting of HF, $AlCl_3$, and solid catalysts of an acidic nature (heterogeneous).

8. The process according to claim 7, wherein said alkylation catalyst is used in quantities ranging from 0.05% to 10% in moles with respect to the olefin, and the molar ratio of said aromatic hydrocarbon/olefin is between 1 and 20.

9. The process according to claim 1, wherein the hydrogenation step (e) takes place with a fixed-bed catalyst selected from the group consisting of metal of group VIII and IVA, of the periodic table, supported on inorganic inert materials selected from the group consisting of alumina, silica, or their mixtures, clays, zeolites, synthetic or natural, in a form selected from the group consisting of of cylinders, spherules, and extruded products.

10. The process according to claim 1 wherein the $C_{10}$–$C_{14}$ n-paraffins are introduced before step (e).

11. The process according to claim 1, wherein said mixture in step (b) consists essentially of linear mono-olefins, non-linear olefins, aromatic by-products, diolefins and non-reacted n-paraffins.

12. The process according to claim 11, wherein said mono-olefins are present in an amount of 10–20% by weight, said non-linear olefins are present in an amount of less than 3% by weight, said aromatic by-products are present in an amount of 0.1–0.7% by weight, and said diolefins are present in an amount of 0.5–3% by weight, based on the weight of said mixture.

13. The process according to claim 1, wherein said selectively hydrogenating is carried out at a temperature of 50–250° C., a pressure of 1–20 kg/cm$^2$, and a space velocity of 0.5–20 h$^{-1}$.

14. The process according to claim 1, wherein, in said selectively hydrogenating, said diolefins are selectively hydrogenated in a conversion yield of up to 100% with a selectivity of up to 90%.

15. The process according to claim 1, wherein said fraction comprising said linear alkylaromatic hydrocarbon resulting from said distilling comprises more than 99% by weight of said linear alkylaromatic hydrocarbon.

16. The process according to claim 1, wherein said fraction comprising said linear alkylaromatic hydrocarbon resulting from said distilling comprises less than 1% by weight of cyclic compounds selected from the group consisting of dialkyltetralines and dialkylindanes.

17. The process according to claim 1, wherein said aromatic hydrocarbon is selected from the group consisting of benzene and toluene.

18. The process according to claim 1, wherein said aromatic by-products comprise at least one selected from the group consisting of alkylbenzenes, polyalkylbenzenes, compounds with tetralinic rings and compounds with naphthalenic rings.

19. The process according to claim 1, wherein, in said hydrogenation step (e), more than 90% of said aromatic by-products are transformed into said cycloparaffins.

20. The process according to claim 1, wherein said hydrogenation step (e) is carried out in a trickle-bed reactor at a pressure of 1–100 kg/cm$^2$, a space velocity of 1–80 h$^{-1}$, and a temperature of 50–500° C.

* * * * *